United States Patent [19]

Saito et al.

[11] Patent Number: 4,831,189

[45] Date of Patent: May 16, 1989

[54] PROCESS FOR PRODUCING AROMATIC DICARBOXYLIC ACIDS

[75] Inventors: Yoshinori Saito, Ichikawa; Shinichi Araki, Tokyo; Yoshio Sugita, Chiba; Naoji Kurata, Nishinomiya, all of Japan

[73] Assignees: Nippon Shokubai Kagaku Kogyo Co. Ltd., Osaka; Nihon Jyoryu Kogyo Co., Ltd., Chiba, both of Japan

[21] Appl. No.: 831,267

[22] Filed: Feb. 20, 1986

[30] Foreign Application Priority Data

Feb. 25, 1985 [JP] Japan .................................. 60-34498
Jun. 14, 1985 [JP] Japan ................................ 60-128291
Jan. 14, 1986 [JP] Japan .................................... 61-4273

[51] Int. Cl.$^4$ ............................................ C07C 51/16
[52] U.S. Cl. .................................................. 562/408
[58] Field of Search ........................................ 562/408

[56] References Cited

U.S. PATENT DOCUMENTS 2,786,076 3/1957 O'Connor et al. ................... 562/408
3,165,547 1/1965 Altpeter et al. ...................... 562/408

FOREIGN PATENT DOCUMENTS 1130801 6/1962 Fed. Rep. of Germany ...... 562/408

*Primary Examiner*—Werren B. Lone
*Attorney, Agent, or Firm*—Sherman and Shalloway

[57] ABSTRACT

A process for producing an aromatic dicarboxylic acid which comprises subjecting a "K-region" arene to liquid phase oxidation with hydrogen peroxide in a water-insoluble organic solvent in the presence of a tungsten compound and a phase transfer catalyst and optionally a mineral acid.

26 Claims, No Drawings

PROCESS FOR PRODUCING AROMATIC DICARBOXYLIC ACIDS

This invention relates to a process for producing an aromatic dicarboxylic acid, and more particularly to a process for producing an aromatic dicarboxylic acid in high yield which comprises subjecting a "K-region" arene to liquid phase oxidation with hydrogen peroxide in a water-insoluble organic solvent in the presence of a tungseen compound and a phase transfer catalyst.

As a method for producing aromatic dicarboxylic acids, e.g. biphenyl-2,2'-dicarboxylic acid, a method is known which comprises subjecting phenanthrene, or 9,10-phenanthrenequinone, an oxidized product of phenanthrene to liquid phase oxidation with chromic acid or a bichromate. There are proposed other methods, i.e. a gaseous phase catalytic oxidation method of phenanthrene using a vanadium-type solid catalyst, and a liquid phase oxidation method such as an oxidation method using a permanganate, an oxidation method in aliphatic organic carboxylic acids using hydrogen peroxide or an organic peroxide and an ozone oxidation method.

Regarding a method for producing phenanthrene-4,5-dicarboxylic acid, there is very little literature, and a method wherein pyrene is oxidized with hydrogen peroxide via ozonolysis is only known [see Bulletin des Societes Chimiques Belges, vol. 72, pp. 289-290, 1963].

The above method for producing biphenyl-2,2'-dicarboxylic acid however suffers the problems to follow. That is, in the method using a chromium compound as an oxidizing agent, discharging of the chromium compound outside the system is severely restricted in the aspects of the pevention of environmental pollution and the environmental health. The use of the chromium compound in a closed system and a higher standard of working environment are therefore required, involving an enormous cost. Not only that, but incorporation of the chromium compound into products is unavoidable. Other methods have also defects that the yield is low, oxidizing agents are expensive and corrosion of apparatuses is unescapable. Consequently, these methods have not come to be effective industrial methods.

In accordance with the foregoing method for producing phenanthrene-4,5-dicarboxylic acid, phenanthrene-4,5-dicarboxylic acid is obtained only in low yield of 28% by ozonizing pyrene and then oxidizing the resulting substance with hydrogen peroxide in a sodium hydroxide-alcohol solvent at a low temperature of −20° C. This method therefore cannot be actually industrialized because of complicated operation and low yield.

The present inventors have made extensive studies on a process for producing aromatic dicarboxylic acids economically advantageously, and as a result found a process wherein aromatic dicarboxylic acids can be produced from "K-region" arenes in high yields.

Thus, the present invention provides a process for producing an aromatic dicarboxylic acid in high yield in a simple manner by subjecting a "K-region" arene to liquid phase oxidation with hydrogen peroxide in a water-insoluble organic solvent in the presence of a tungsten compound and a phase transfer catalyst and optionally a mineral acid.

Most of the "K-region" arenes used in this invention are compounds obtained from coal tar or derivatives thereof. The starting material in the process of this invention is preferably at least one compound selected from the group consisting of phenanthrene, pyrene, benzo[a]pyrene, benz[a]anthracene, benz[a,h]anthracene, chrysene and o-phenanthroline. Preferably, the "K-region" arenes have high purity, but considering economics the purity may be more than 80%, specifically more than 90%. This is because even if products obtained by oxidizing impurities of the "K-region" arenes with hydrogen peroxide are partially incorporated into the resulting aromatic dicarboxylic acids, they can easily be removed, if necessary, by a simple purification step.

The tungsten compound used in this invention is preferably an oxygen-containing hexavalent tungsten compound. Examples of said compound are tungstic acid and alkali salts (e.g. sodium salts and potassium salts) and ammonium salts thereof.

When phenanthrene is used as a starting material in the process of this invention, heteropoly-acid tungsten compounds such as phosphotungstic acid, silicotungstic acid, arsenotungstic acid, stannotungstic acid, germanotungstic acid, and alkali metal salts and ammonium salts of these compounds are also available as the tungsten compound.

These tungsten compounds can be used such that they are dissolved or partially suspended in a reaction solution. The amount of the tungsten compound used is 0.005 to 0.2 gram atom, preferably 0.01 to 0.1 gram atom, as a tungsten atom, per mol of the "K-region" arene. Where the amount is less than 0.01 gram atom, the oxidation reaction does not proceed enough. Where the amount is more than 0.1 gram atom, decomposition of hydrogen peroxide goes drastic, inviting a disadvantage of losing the efficiency of hydrogen peroxide.

The phase transfer catalyst used in this invention is at least one substance selected from the group consisting of quaternary ammonium salts, quaternary phosphonium salts, quaternary arsonium salts, tertiary amines, tertiary phosphines and tertiary arsines. Examples of the quaternary ammonium salts are trimethylalkylammonium halides, trialkylmethylammonium halides and pyridinium compounds. Most preferable are alkyltrimethylammonium chlorides, trialkylmethylammonium chlorides and alkylpyridinium chlorides wherein the number of carbon atoms of alkyl groups is 8 to 18. Examples of the quaternary phosphonium salts are alkyl triphenylphosphonium halides. Examples of the quaternary arsonium salts are alkyltriphenylarsonium halides. Examples of the tertiary amines are trialkylamines and methyldialkylamines. Most preferable are trialkylamines and methyldialkylamines wherein the number of carbon atoms of alkyl groups is 4 to 18. Examples of the tertiary phosphines are trialkylphosphines. Examples of the tertiary arsines are trialkylarsines. The amount of the phase transfer catalyst is 0.2 to 5 mol, preferably 0.5 to 2 mol per gram atom of tungsten.

It has been found for the first time that in producing the aromatic dicarboxylic acids by the oxidation of the "K-region" arenes with hydrogen peroxide, the use of tungsten compounds alone as the catalyst does not allow the oxidation reaction, but when the phase transfer catalyst is co-existent, the oxidation reaction smoothly advances, and the "K-region" arenes are converted into aromatic dicarboxylic acids in high selectivity.

In this invention, when the "K-region" arene is oxidized with hydrogen peroxide in the water-insoluble organic solvent in the presence of the tungsten compound as the catalyst and the phase transfer catalyst, controlling an acidity in the reaction system has a serious influence on the progress of the oxidation reaction. That is, where the reaction is further performed in an acid zone by causing a mineral acid to exist, conversion of the "K-region" arene into the aromatic dicarboxylic acid is expedited, thereby lessening the amount of hydrogen peroxide used. The mineral acid used is at least one compound selected from the group consisting of sulfuric acid, phosphoric acid and arsenic acid. The amount of the mineral acid is 0.1 to 20 mols per gram atom of tungsten.

The water-insoluble organic solvent may be any solvent substantially immiscible with an aqueous phase containing hydrogen peroxide and inactive in the reaction system. Examples of said solvent are aliphatic hydrocarbons, alicyclic hydrocarbons, aromatic hydrocarbons, and halogenated substances and esters of these hydrocarbons. Especially, the aliphatic hydrocarbons, aromatic hydrocarbons and halogenated substances of these hydrocarbons are preferable. The amount of the water-insoluble organic solvent is 0.5 to 10 parts by weight, preferably 1 to 5 part by weight per part by weight of the "K-region" arene considering the stirring conditions during the oxidation reaction, solubility of the resulting aromatic dicarboxylic acid in the water-insoluble organic solvent and withdrawing of the aromatic dicarboxylic acid precipitated.

A hydrogen peroxide aqueous solution in any concentration is available as hydrogen peroxide. Taking account of the fact that as the concentration is higher the oxidation reaction proceeds more smoothly, as well as of the handling and the availability of commercial products, the hydrogen peroxide aqueous solution is used in a concentration of 20 to 90%, preferably 40 to 70%. The amount of hydrogen peroxide may be more than a stoichiometric amount because the "K-region" arene consumed is converted into the aromatic dicarboxylic acid in high selectivity. It is usually 4 to 30 mols, preferably 6 to 10 mols per mol of the "K-region" arene.

The reaction can be performed at temperatures in the range of room temperature to 120° C. In consideration of the control of the oxidation reaction and the reaction time, the reaction temperature is commonly selected from the range of 50 to 100° C. The reaction time is usually 1 to 20 hours. The pressure in the reaction system may be an increased pressure, a normal pressure or a pressure lower than atmospheric pressure. The reaction can be carried out either batchwise or continuously.

The tungsten compounds and other transition metal compounds are known as effective catalysts for hydroxylation, epoxidation and carboxylation with oxidative cleavage of varied organic compounds using hydrogen peroxide, organic peracids or peroxides as an oxidizing agent. However, a process that can produce aromatic dicarboxylic acids in high yields and high selectivity from "K-region" arenes such as phenanthrene, pyrene, etc. using these catalysts has not yet been known. The present invention has enabled this process for the first time by oxidizing the "K-region" arene with hydrogen peroxide in the water-insoluble organic solvent using the tungsten compound as the catalyst in combination with the phase transfer catalyst. It has moreover brought forth such dramatic effects that the convertion of the "K-Region" arene into the aromatic dicarboxylic acid is rapidly improved by causing the mineral acid to exist in the reaction system for controlling the reaction in the acid zone, and the aromatic dicarboxylic acid is afforded in quite high yield.

The process of this invention is, though not restrained by a principle, presumed to be such that the tungsten compound as one component of the catalyst is converted into a water-soluble tungsten peroxide by decomposition with hydrogen peroxide and in a non-uniform phase composed of an aqueous phase containing those substances and an oily phase containing a substantially immiscible inactive organic solvent and the "K-region" arene, the active oxygen of tungsten peroxide serves to oxidize the "K-region" arene by the action of the phase transition catalyst, thereby facilitating the conversion of the "K-region" arene into the aromatic dicarboxylic acid. In case the reaction system is controlled in the acid zone by causing a mineral acid such as sulfuric acid, phosphoric acid or arsenic acid to exist in the reaction system, the decomposition of hydrogen peroxide is slowed down and the ability of the phase transfer catalyst in the non-uniform phase increases.

According to this invention, the "K-region" arene is converted into the aromatic dicarboxylic acid in high selectivity by the oxidation with hydrogen peroxide, and as a result crystals of the aromatic dicarboxylic acid can be afforded in high yield and high purity only by simple steps of cooling and separation by filtration after termination of the reaction. Moreover, in order to remove oxides derived from impurities of the starting "K-region" arene and contained in the resulting crystals, said crystals are, if necessary, extracted with an alkali aqueous solution by suspending or dissolving in an organic solvent, precipitated with an acid, separated by filtration and dried. The aromatic dicarboxylic acid in high purity of more than 99% can be obtained with little loss by the foregoing simple operation.

The following Examples illustrate this invention more specifically. However, this invention is, of course, not limited to said Examples.

In said Examples, the conversion of phenanthrene, the selectivity to biphenyl-2,2'-dicarboxylic acid, the conversion of pyrene and the selectivity to phenanthrene-4,5-dicarboxylic acid are found by the following equations.

$$\text{Conversion of phenanthrene (\%)} = \frac{\text{Amount of phenanthrene consumed (mol)}}{\text{Amount of phenanthrene charged (mol)}} \times 100$$

$$\text{Selectivity to biphenyl-2,2'-dicarboxylic acid (\%)} = \frac{\text{Amount of biphenyl-2,2'-dicarboxylic acid formed (mol)}}{\text{Amount of phenanthrene consumed (mol)}} \times 100$$

$$\text{Conversion of pyrene (\%)} = \frac{\text{Amount of pyrene consumed (mol)}}{\text{Amount of pyrene charged (mol)}} \times 100$$

$$\text{Selectivity to phenanthrene-4,5-dicarboxylic acid (\%)} = \frac{\text{Amount of phenanthrene-4,5-dicarboxylic acid formed (mol)}}{\text{Amount of pyrene consumed (mol)}} \times 100$$

EXAMPLE 1

25.0 g of 90.6% phenanthrene, 1.27 g of tungstic acid, 2.05 g of tri-n-octylmethylammonium chloride and 38 g of monochlorobenzene were charged into a 300 cc four-necked round bottom glass flask fitted with a thermometer, a cooler and a stirrer, and heated to 80° C. in a hot bath with vigorous stirring. Subsequently, 143.4 g of a 60.2% hydrogen peroxide aqueous solution was added dropwise with a glass dropping funnel over the course of 30 minutes, and the mixture was maintained for 6 hours. During that period, the pH of the reaction solution was 0.5 or less.

After the reaction terminated, the content was analyzed by high performance liquid chromatography and gas chromatography. The results are as follows.

| Conversion of phenanthrene | 39.0% |
|---|---|
| Selectivity to biphenyl-2,2'-dicarboxylic acid | 97.2% |

EXAMPLE 2

The procedure in Example 1 was followed except using 1.34 g of lauryltrimethylammonium chloride instead of tri-n-octylmethylammonium chloride. During the reaction, the pH of the reaction solution was 1.1 or less.

| Conversion of phenanthrene | 31.8% |
|---|---|
| Selectivity to biphenyl-2,2'-dicarboxylic acid | 97.5% |

EXAMPLE 3

The procedure in Example 1 was followed except using 1.44 g of laurylpyridinium chloride instead of tri-n-octylmethylammonium chloride. During the reaction, the pH of the reaction solution was 3.5 or less.

| Conversion of phenanthrene | 21.3% |
|---|---|
| Selectivity to biphenyl-2,2'-dicarboxylic acid | 98.2% |

EXAMPLE 4

The procedure in Example 1 was followed except using 2.28 g of triphenylmethylarsonium iodide instead of tri-n-octylmethylammonium chloride. During the reaction, the pH of the reaction solution was 6.6 or less.

| Conversion of phenanthrene | 17.8% |
|---|---|
| Selectivity to biphenyl-2,2'-dicarboxylic acid | 97.7% |

EXAMPLE 5

The procedure in Example 1 was followed except that the amount of tungstic acid was changed into 1.59 g and 2.25 g of tri-n-octylamine was used instead of tri-n-octylmethylammonium chloride. During the reaction, the pH of the reaction solution was 1.1 or less.

| Conversion of phenanthrene | 73.7% |
|---|---|
| Selectivity of biphenyl-2,2'-dicarboxylic acid | 95.7% |

EXAMPLE 6

The procedure in Example 5 was repeated except that 1.62 g of N-methyl-di-n-octylamine was used instead of tri-n-octylamine. During the reaction, the pH of the reaction solution was 1.1 or less.

| Conversion of phenanthrene | 76.2% |
|---|---|
| Selectivity to biphenyl-2,2'-dicarboxylic acid | 96.0% |

EXAMPLE 7

The procedure in Example 5 was repeated except that 2.35 g of tri-n-octylphosphine was used instead of tri-n-octylamine. During the reaction, the pH of the reaction solution was 1.4 or less.

| Conversion of phenanthrene | 65.0% |
|---|---|
| Selectivity to biphenyl-2,2'-dicarboxylic acid | 92.2% |

EXAMPLE 8

The procedure in Example 1 was repeated except that 25.0 g of 92.3% pyrene was used instead of phenanthrene, and the amount of tungstic acid was changed into 1.14 g, the amount of tri-n-octylmethylammonium chloride into 1.84 g, the amount of monochlorobenzene into 67 g and the amount of the 60.2% hydrogen peroxide aqueous solution into 128.7 g respectively. During the reaction, the pH of the reaction solution was 2.2 or less.

| Conversion of pyrene | 43.2% |
|---|---|
| Selectivity to phenanthrene-4,5-dicarboxylic acid | 78.6% |

EXAMPLE 9

The procedure in Example 8 was repeated except that 1.20 g of lauryltrimethylammonium chloride was used instead of tri-n-octylmethylammonium chloride. During the reaction, the pH of the reaction solution was 2.5 or less.

| Conversion of pyrene | 35.7% |
|---|---|
| Selectivity to phenanthrene-4,5-dicarboxylic acid | 74.2% | cl EXAMPLE 10

The procedure in Example 8 was repeated except that 1.29 g of laurylpyridinium chloride was used instead of tri-n-octylmethylammonium chloride. During the reaction, the pH of the reaction solution was 3.8 or less.

| Conversion of pyrene | 26.4% |
|---|---|
| Selectivity to phenanthrene-4,5-dicarboxylic acid | 73.0% |

EXAMPLE 11

The procedure in Example 8 was repeated except that 2.05 g of triphenylmethylarsonium iodide was used instead of tri-n-octylmethylammonium chloride. During the reaction, the pH of the reaction solution was 6.2 or less.

| Conversion of pyrene | 20.7% |
|---|---|
| Selectivity to | 71.3% | phenanthrene-4,5-dicarboxylic acid

EXAMPLE 12

The procedure in Example 8 was repeated except that the amount of rungstic acid was changed into 1.42 g and 2.02 g of tri-n-octylamine was used instead of tri-n-octylmethylammonium chlorde. During the reaction, the pH of the reaction solution was 1.9 or less.

| | |
|---|---|
| Conversion of pyrene | 85.0% |
| Selectivity to phenanthrene-4,5-dicarboxylic acid | 74.8% |

EXAMPLE 13

The procedure in Example 12 was repeated except that 1.46 g of N-methyl-di-n-octylamine was used instead of tri-n-octylamine. During the reaction, the pH of the reaction solution was 1.8 or less.

| | |
|---|---|
| Conversion of pyrene | 83.6% |
| Selectivity to phenanthrene-4,5-dicarboxylic acid | 75.4% |

EXAMPLE 14

25.0 g of 90.6% phenanthrene, 1.27 g of tungstic acid, 2.05 g of tri-n-octylmethylammonium chloride, 1.2 cc of 10% phosphoric acid and 38 g of monochlorobenzene were charged into a 300 cc four-necked round bottom glass flask fitted with a thermometer, a cooler and a stirrer, and heated to 80° C. in a hot bath with vigorous stirring. 50.2 g of a 60.2% hydrogen peroxide aqueous solution was then added dropwise from a glass dropping funnel over the course of 30 minutes, and the mixture was maintained for 6 hours. During that period, the pH of the reaction solution was 0.5 or less. The subsequent operation was performed in the same way as in Example 1.

| | |
|---|---|
| Conversion of phenanthrene | 99.6% |
| Selectivity to biphenyl-2,2'-dicarboxylic acid | 99.1% |

EXAMPLE 15

The procedure in Example 14 was followed except that 0.3 cc of 60% arsenic acid was used instead of 10% phosphoric acid. During the reaction, the pH of the reaction solution was 0.5 or less.

| | |
|---|---|
| Conversion of phenanthrene | 98.8% |
| Selectivity to biphenyl-2,2'-dicarboxylic acid | 99.4% |

EXAMPLE 16

The procedure in Example 14 was followed except that 8 cc of 30% sulfuric acid was used instead of 10% phosphoric acid. During the reaction, the pH of the reaction solution was 0.5 or less.

| | |
|---|---|
| Conversion of phenanthrene | 75.7% |
| Selectivity to biphenyl-2,2'-dicarboxylic acid | 98.3% |

EXAMPLE 17

The procedure in Example 14 was followed except that 1.34 g of lauryltrimethylammonium chloride was used instead of tri-n-octylmethylammonium chloride. During the reaction, the pH of the reaction solution was 0.5 or less.

| | |
|---|---|
| Conversion of phenanthrene | 97.9% |
| Selectivity to biphenyl-2,2'-dicarboxylic acid | 98.8% |

EXAMPLE 18

The procedure in Example 14 was followed except that 1.68 g of sodium tungstate dihydrate was used instead of tungstic acid and the amount of 10% phosphoric acid was changed into 4 cc. During the reaction, the pH of the reaction solution was 0.9 or less.

| | |
|---|---|
| Conversion of phenanthrene | 93.2% |
| Selectivity to biphenyl-2,2'-dicarboxylic acid | 97.6% |

EXAMPLE 19

The procedure in Example 18 was followed except that 8 cc of 30% sulfuric acid was used instead of 10% phosphoric acid. During the reaction, the pH of the reaction solution was 1.2 or less.

| | |
|---|---|
| Conversion of phenanthrene | 63.2% |
| Selectivity to biphenyl-2,2'-dicarboxylic acid | 97.8% |

EXAMPLE 20

The procedure in Example 18 was followed except that 1.33 g of ammonium paratungstate was used instead of sodium tungstate dihydrate. During the reaction, the pH of the reaction solution was 0.9 or less.

| | |
|---|---|
| Conversion of phenanthrene | 97.5% |
| Selectivity to biphenyl-2,2'-dicarboxylic acid | 98.3% |

EXAMPLE 21

The procedure in Example 14 was followed except that the amount of tungstic acid was changed into 1.59 g, 2.25 g of tri-n-octylamine was used instead of tri-n-octylmethylammonium chloride and the amount of 10% phosphoric acid was changed into 1.5 cc. During the reaction, the pH of the reaction solution was 0.8 or less.

| | |
|---|---|
| Conversion of phenanthrene | 96.1% |
| Selectivity to | 98.9% |

-continued

| biphenyl-2,2'-dicarboxylic acid |

EXAMPLE 22

The procedure in Example 21 was followed except that 1.62 g of N-methyl-di-n-octylamine was used instead of tri-n-octylamine. During the reaction, the pH of the reaction solution was 0.9 or less.

| | |
|---|---|
| Conversion of phenanthrene | 98.4% |
| Selectivity to biphenyl-2,2'-dicarboxylic acid | 98.2% |

EXAMPLE 23

The procedure in Example 21 was followed except that 0.4 cc of 60% arsenic acid was used instead of 10% phosphoric acid. During the reaction, the pH of the reaction solution was 1.0 or less.

| | |
|---|---|
| Conversion of phenanthrene | 88.8% |
| Selectivity to biphenyl-2,2'-dicarboxylic acid | 94.7% |

EXAMPLE 24

The procedure in Example 21 was followed except that 8 cc of 30% sulfuric acid was used instead of 10% phosphoric acid. During the reaction, the pH of the reaction solution was 0.7 or less.

| | |
|---|---|
| Conversion of phenanthrene | 91.2% |
| Selectivity to biphenyl-2,2'-dicarboxylic acid | 96.2% |

EXAMPLE 25

The procedure in Example 24 was followed except that 2.09 g of sodium tungstate dihydrate was used instead of tungstic acid. During the reaction, the pH of the reaction solution was 0.8 or less.

| | |
|---|---|
| Conversion of phenanthrene | 87.9% |
| Selectivity to biphenyl-2,2'-dicarboxylic acid | 94.6% |

EXAMPLE 26

The procedure in Example 21 was followed except that 1.60 g of ammonium paratungstate was used instead of tungstic acid and the amount of 10% phosphoric acid was changed into 6 cc. During the reaction, the pH of the reaction solution was 1.5 or less.

| | |
|---|---|
| Conversion of phenanthrene | 85.0% |
| Selectivity to biphenyl-2,2'-dicarboxylic acid | 95.1% |

EXAMPLE 27

The procedure in Example 16 was followed except that 25.0 g of 92.3% pyrene was used instead of phenanthrene, and the amount of tungstic acid was chaneed into 1.14 g, the amount of tri-n-octylmethylammonium chloride into 1.84 g, the amount of monochlorobenzene into 67 g and the amount of the 60.2% hydrogen peroxide aquous solution into 45.1 g respectively. During the reaction, the pH of the reaction solution was 1.4 or less.

| | |
|---|---|
| Conversion of pyrene | 93.0% |
| Selectivity to phenanthrene-4,5-dicarboxylic acid | 70.5% |

EXAMPLE 28

The procedure in Example 27 was followed except that 0.3 cc of 60% arsenic acid was used instead of 30% sulfuric acid. During the reaction, the pH of the reaction solution was 1.4 or less.

| | |
|---|---|
| Conversion of pyrene | 98.4% |
| Selectivity to phenanthrene-4,5-dicarboxylic acid | 78.8% |

EXAMPLE 29

The procedure in Example 27 was followed except that 1.1 cc of 10% phosphoric acid was used instead of 30% sulfuric acid. During the reaction, the pH of the reaction solution was 0.7 or less.

| | |
|---|---|
| Conversion of pyrene | 99.2% |
| Selectivity to phenanthrene-4,5-dicarboxylic acid | 81.3% |

EXAMPLE 30

The procedure in Example 29 was followed except that 1.20 g of laurylmethylammonium chloride was used instead of tri-n-octylmethylammonium chloride. During the reaction, the pH of the reaction solution was 2.0 or less.

| | |
|---|---|
| Conversion of pyrene | 92.5% |
| Selectivity to phenanthrene-4,5-dicarboxylic acid | 78.9% |

EXAMPLE 31

The procedure in Example 29 was followed except that 1.51 g of sodium tungstate dihydrate was used instead of tungstic acid and the amount of 10% phosphoric acid was changed into 4 cc. During the reaction, the pH of the reaction solution was 1.9 or less.

| | |
|---|---|
| Conversion of pyrene | 92.2% |
| Selectivity to phenanthrene-4,5-dicarboxylic acid | 80.7% |

EXAMPLE 32

The procedure in Example 27 was followed except that 1.51 g of sodium tungstate dihydrate was used instead of tungstic acid. During the reaction, the pH of the reaction solution was 2.3 or less.

| | |
|---|---|
| Conversion of pyrene | 64.1% |
| Selectivity to phenanthrene-4,5-dicarboxylic acid | 73.8% |

EXAMPLE 33

The procedure in Example 31 was followed except that 1.17 g of ammonium paratungstate was used instead of sodium tungstate dihydrate. During the reaction, the pH of the reaction solution was 1.5 or less.

| | |
|---|---|
| Conversion of pyrene | 95.4% |
| Selectivity to phenanthrene-4,5-dicarboxylic acid | 79.5% |

EXAMPLE 34

The procedure in Example 29 was followed except that the amount of tungstic acid was changed into 1.42 g, 2.02 g of tri-n-octylamine was used instead of tri-n-octylmethylammonium chloride, and the amount of 10% phosphoric acid was changed into 1.4 cc. During the reaction, the pH of the reaction solution was 1.5 or less.

| | |
|---|---|
| Conversion of pyrene | 97.1% |
| Selectivity to phenanthrene-4,5-dicarboxylic acid | 80.6% |

EXAMPLE 35

The procedure in Example 34 was followed except that 1.46 g of N-methyl-di-n-octylamine was used instead of tri-n-octylamine and 8 cc of 30% sulfuric acid instead of 10% phosphoric acid, respectively. During the reaction, the pH of the reaction solution was 1.6 or less.

| | |
|---|---|
| Conversion of pyrene | 88.0% |
| Selectivity to phenanthrene-4,5-dicarboxylic acid | 72.7% |

What we claim is:

1. A process for producing an aromatic dicarboxylic acid which comprises subjecting a "K-region" arene selected from the group consisting of phenanthrene, pyrene, benzo(a)pyrene, benz(a)anthracene, dibenz(a,h-)anthracene, chrysene, o-phenanthroline and mixtures thereof to liquid phase oxidation with hydrogen peroxide in a water-insoluble organic solvent in the presence of tungstic acid or an alkali metal salt or ammonium salt thereof and a phase transfer catalyst.

2. The process of claim 1 wherein the tungsten compound is used in an amount of 0.005 to 0.2 gram atom, as a tungsten atom, per mol of the "K-region" arene.

3. The process of claim 1 wherein the phase transfer catalyst is at least one substance selected from the group consisting of quaternary ammonium salts, quaternary phosphonium salts, quaternary arsonium salts, tertiary amines, tertiary phosphines and tertiary arsines, and is used in an amount of 0.2 to 5 mol per gram atom of tungsten.

4. The process of claim 1 wherein the water-insoluble organic solvent is selected from the group consisting of aliphatic hydrocarbons, aromatic hydrocarbons and halogenated substances of these hydrocarbons, and is used in an amount of 0.5 to 10 parts by weight per part by weight of the "K-region" arene.

5. The process of claim 1 wherein the aromatic dicarboxylic acid is biphenyl-2,2'-dicarboxylic acid or phenanthrene-4,5-dicarboxylic acid.

6. The process of claim 1 for producing biphenyl-2,2'-dicarboxylic acid from phenanthrene as the "K-region" arene.

7. The process of claim 1 for producing phenanthrene-4,5-dicarboxylic acid from pyrene as the "K-region" arene.

8. The process of claim 1 wherein the tungsten compound is used in an amount of 0.01 to 0.1 gram atom, as tungsten, per mole of the "K-region" arene.

9. The process of claim 1 wherein the phase transfer catalyst is alkyl trimethyl ammonium chloride, trialkylmethyl ammonium chloride, or alkylpyridinium chloride, wherein the alkyl has from 8 to 18 carbon atoms.

10. The process of claim 1 wherein the phase transfer catalyst is an alkyltriphenylphosphonium halide or alkyltriphenylarsonium halide.

11. The process of claim 1 wherein the phase trassfer catalyst is trialkylamine or methyldialkylamine, wherein the alkyl has from 4 to 18 carbon atoms.

12. The process of claim 1 wherein the phase transfer catalyst is a trialkylphosphine or trialkylarsine.

13. A process for producing an aromatic dicarboxylic acid which comprises subjecting a "K-region" arene selected from the group consisting of phenanthrene, pyrene, benzo(a)pyrene, benz(a)anthracene, dibenz(a,h-)anthracene, chrysene, o-phenanthroline and mixtures thereof to liquid phase oxidation with hydrogen peroxide in an acid zone in a water-insoluble organic solvent and in the presence of a mineral acid, tungstic acid or an alkali metal salt or ammonium salt thereof and a phase transfer catalyst.

14. The process of claim 13 wherein the phase transfer catalyst is at least one substance selected from the group consisting of quaternary ammonium salts, quaternary phosphonium salts, quaternary arsonium salts, tertiary amines, tertiary phosphines and tertiary arsines, and is used in an amount of 0.2 to 5 mol per gram atom of tungsten.

15. The process of claim 13 wherein the water-insoluble organic solvent is selected from aliphatic hydrocarbons, aromatic hydrocarbons and halogenated substances of these hydrocarbons, and is used in an amount of 0.5 to 10 parts by weight per part by weight of the "K-region" arene.

16. The process of claim 13 wherein the mineral acid is at least one compound selected from the group consisting of sulfuric acid, phosphoric acid and arsenic acid, and is used in an amount of 0.1 to 20 mols per gram atom of tungsten.

17. The process of claim 13 wherein the aromatic dicarboxylic acid is biphenyl-2,2,-dicarboxylic acid or phenanthrene-4,5-dicarboxylic acid.

18. The process of claim 13 for producing biphenyl-2,2'-dicarboxylic acid from phenanthrene as the "K-region" arene.

19. The process of claim 13 for producing phenanthrene-4,5-dicarboxylic acid from pyrene as the "K-region" arene.

20. The process of claim 13 wherein the tungsten compound is used in an amount of 0.0 to 0.1 gram atom, as tungsten, per mol of the "K-region" arene.

21. The process of claim 13 wherein the phase transfer catalyst is alkyl trimethyl ammonium chloride, trialkylmethyl ammonium chloride, or alkylpyridinium chloride, wherein the alkyl has from 8 to 18 carbon atoms.

22. The process of claim 13 wherein the phase transfer catalyst is an alkyltriphenylphosphonium halide or alkyltriphenylarsonium halide.

23. The process of claim 13 wherein the phase transfer catalyst is trialkylamine or methyldialkylamine, wherein the alkyl has from 4 to 18 atoms.

24. The process of claim 13 wherein the phase transfer catalyst is a trialkylphosphine or trialkylarsine.

25. A process for producing an aromatic dicarboxylic acid which comprises subjecting a "K-region" arene selected from the group consisting of phenanthrene, pyrene, benzo(a)pyrene, benz(a)anthracene, dibenz(a,h-)anthracene, chrysene, o-phenanthroline and mixtures thereof to liquid phase oxidation with hydrogen peroxide in an acid zone in a water-insoluble organic solvent in the presence of a mineral acid, at least one tungsten compound selected from the group consisting of tungstic acid, and sodium salts, potassium salts and ammonium salts thereof, used in an amount of 0.005 to 0.2 gram atom, as a tungsten atom, per mol of the "K-region" arene and a phase transfer catalyst.

26. A process for producing an aromatic dicarboxylic acid which comprises subjecting a "K-region" arene selected from the group consisting of phenanthrene and pyrene to liquid phase oxidation at a temperature of from room temperature to about 120° C. with from 4 to 30 mols of hydrogen peroxide, per mole of the "K-region" arene, in an aliphatic hydrocarbon, halogenated aliphatic hydrocarbon, aromatic hydrocarbon or halogenated aromatic hydrocarbon as a water-insoluble organic solvent, in the presence of tungstic acid, or alkali metal or ammonium salt thereof, in an amount of 0.01 to 0.1 gram atom, as tungsten, per mol of the "K-region" arene, a phase transfer catalyst selected from the group consisting of quaternary ammonium salts, quaternary phosphonium salts, quaternary arsonium salts, tertiary amines, tertiary phosphines, tertiary arsines and mixtures thereof, in an amount of 0.2 to 5 mol per gram atom of tungsten, and up to 20 mols per gram atom of tungsten of sulfuric acid, phosphoric acid, arsenic acid or mixtures thereof.

* * * * *

UNITED STATES PATENT AND TRADEMARK OFFICE
CERTIFICATE OF CORRECTION

PATENT NO. : 4,831,189
DATED : May 16, 1989
INVENTOR(S) : YOSHINORI SAITO ET AL.

It is certified that error appears in the above-identified patent and that said Letters Patent is hereby corrected as shown below:

Claim 11, line 1 of the claim, "trassfer" should read --transfer--.

Claim 17, line 2 of the claim, "biphenyl-2,2,-dicarboxylic" should read --biphenyl-2,2'-dicarboxylic--.

Claim 20, line 2 of the claim, "0.0" should read --0.01--.

Signed and Sealed this

Ninth Day of January, 1990

Attest:

JEFFREY M. SAMUELS

Attesting Officer     Acting Commissioner of Patents and Trademarks